United States Patent
Phelps et al.

(10) Patent No.: US 7,941,908 B2
(45) Date of Patent: May 17, 2011

(54) METHOD FOR SCALABLE MANUFACTURING OF MEDICAL DIAGNOSTIC ULTRASOUND IMAGING SYSTEMS

(75) Inventors: Robert N. Phelps, Fall City, WA (US);
David A. Petersen, Fall City, WA (US);
John C. Lazenby, Fall City, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 125 days.

(21) Appl. No.: 12/234,470

(22) Filed: Sep. 19, 2008

(65) Prior Publication Data

US 2009/0007414 A1 Jan. 8, 2009

Related U.S. Application Data

(62) Division of application No. 11/169,357, filed on Jun. 28, 2005, now abandoned.

(51) Int. Cl.
*H04R 31/00* (2006.01)

(52) U.S. Cl. .......... 29/594; 29/602.1; 29/609.1; 29/856; 29/868; 310/311; 310/333; 310/334; 310/337; 310/357; 347/54; 347/68; 347/69; 347/70; 347/71; 600/437

(58) Field of Classification Search .................. 29/592.1, 29/594, 602.1, 609, 609.1, 856, 868; 310/311, 310/333–337, 357, 367; 347/54, 68–72; 600/437
See application file for complete search history.

(56) References Cited

U.S. PATENT DOCUMENTS

| | | | |
|---|---|---|---|
| 5,369,624 A | 11/1994 | Fukukita et al. | |
| 5,388,079 A | 2/1995 | Kim et al. | |
| 5,501,219 A | 3/1996 | Phelps et al. | |
| 5,544,128 A | 8/1996 | Kim et al. | |
| 5,573,001 A | 11/1996 | Petrofsky et al. | |
| 6,126,602 A | 10/2000 | Savord | |
| 6,142,946 A | 11/2000 | Hwang et al. | |
| 6,186,948 B1 * | 2/2001 | Kamiyama et al. | 600/443 |
| 6,524,245 B1 * | 2/2003 | Rock et al. | 600/437 |
| 6,530,887 B1 | 3/2003 | Gilbert et al. | |
| 6,783,493 B2 | 8/2004 | Chiang et al. | |
| 2004/0068188 A1 | 4/2004 | Robinson | |
| 2005/0148873 A1 | 7/2005 | Petersen et al. | |
| 2005/0148878 A1 | 7/2005 | Phelps et al. | |
| 2005/0203392 A1 | 9/2005 | Petersen | |
| 2005/0243812 A1 | 11/2005 | Phelps | |
| 2007/0016023 A1 | 1/2007 | Phelps et al. | |

OTHER PUBLICATIONS

Langlois, Portable Ultrasound on Deployment, Sep. 2003, ADF Health, vol. 4.

* cited by examiner

*Primary Examiner* — Paul D Kim

(57) ABSTRACT

A plurality of application specific integrated circuit (ASIC) chips with different functions is provided. Each of the ASICs performs one or more functions along an ultrasound data path. The chips include communications protocols or processes for allowing scaling. For example, ASICs for backend processing include data exchange ports for communicating between other ASICs of the same type. As another example, receive beamformer ASICs cascade for beamformation. By providing ASICs implementing many or most of the ultrasound data path functions, with scalability, the same ASICs may be used for different system designs. A family of systems from high end to low-end using the same types of ASICs, but in different configurations, is provided.

19 Claims, 3 Drawing Sheets

METHOD FOR SCALABLE MANUFACTURING OF MEDICAL DIAGNOSTIC ULTRASOUND IMAGING SYSTEMS

RELATED APPLICATIONS

The present patent document is a divisional of U.S. Published Patent Application No. 20070016023 (Ser. No. 11/169,357), filed Jun. 28, 2005 now abandoned, which is hereby incorporated by reference.

BACKGROUND

The present embodiments relate to medical diagnostic ultrasound systems. In particular, common application specific integrated circuits (ASICs) are provided.

Medical diagnostic ultrasound systems include ultrasound data processing paths. Ultrasound data processing paths include transmit beamformers, receive beamformers, detectors, scan converters, image processors and other stages. The ultrasound data path acquires ultrasound data and generates an image from the ultrasound data. Typically, an ultrasound data path used for any given type of system is independently designed. Low cost systems have different bandwidth, power consumption, features or other characteristics as compared to high cost systems.

Within a given system, a given ASIC may be used multiple times. For example, a receive beamforming ASIC is designed for operation with a limited number of channels, such as 8 or 16 channels. By providing a plurality of these ASICs in parallel, an ultrasound imaging system with a larger number of channels is provided. For low cost systems, the ASICs may be simple. For high cost systems, different ASICs are used. For example, U.S. Pat. No. 5,675,554 provides ASICs capable of different bandwidths as a number of different simultaneous beams are formed. Cascaded summation is then provided to beamformer across the plurality of ASICs.

A same type of ASIC may be used in different products. For example, two different manufacturers use a same system for different products or brand names. Since the systems are the same, providing the same capabilities within the hardware, the same ASICs are used. When a new system is designed, new ASICs are developed. However, the design of new ASICs is expensive and time consuming.

BRIEF SUMMARY

By way of introduction, the preferred embodiments described below include methods and systems for scalable ultrasound imaging systems. A plurality of application specific integrated circuit chips with different functions is provided. Each of the ASICs perform one or more functions along an ultrasound data path. The chips include communications protocols or processes for allowing scaling. For example, ASICs for backend processing include data exchange ports for communicating between other ASICs of the same type. As another example, receive beamformer ASICs cascade for beamformation. By providing ASICs implementing many or most of the ultrasound data path functions, with scalability, the same ASICs may be used for different system designs. A family of systems from high end to low-end using the same ASICs, but in different configurations, is provided.

In one example of scalability, a receive beamformer ASIC is operable to determine spatial coordinates associated with a given beam along a straight line using real-time time of flight calculations. More complex systems include more advanced coordinate capabilities. Where multiple beams are received simultaneously, the spatial coordinates associated with the beams may be along a non-straight line. Similarly, Gaussian wavefronts or aberrations may contribute to receiving along spatial coordinates along a non-straight line. A wavefront calculator is provided in addition to the real-time time of flight calculator to implement the additional functionality in a high cost system. The wavefront calculator changes the acoustic sample coordinates used by the received beamformer. The time of flight calculator then calculates distances to the changed acoustic sample coordinates.

In a first aspect, a scalable system is provided for receive beamforming with ultrasound. A real-time time of flight of calculator is operable to determine distances to acoustic sample coordinates. A wavefront calculator is operable to change to the acoustic sample coordinates to positions along a non-straight line. A receive beamformer is operable to form acoustic samples as a function of the distances.

In a second aspect, a scalable system is provided for medical diagnostic ultrasound imaging. A first type of integrated circuit is operable to perform a first function along an ultrasound data path. The first type of integrated circuit is operable with one or more of the first type of integrated circuits substantially in parallel relative to the ultrasound data path. A second type of integrated circuit is operable to perform a second function along the ultrasound data path. The second function is responsive to data output by the first type of integrated circuit. The ultrasound data path has at least two different levels of complexity. A first level is associated with a lower cost medical diagnostic ultrasound system and a fewer number of the first type of integrated circuits. A second complexity level is associated with a higher cost medical diagnostic ultrasound system and a greater number of the type of integrated circuits.

In a third aspect, a method is provided for scalable manufacturing of medical diagnostic ultrasound imaging systems. A first set of application-specific integrated circuit chips having ultrasound functions is provided. A second set of application-specific integrated circuit chips is assembled from the first set for a first type of medical diagnostic ultrasound imaging system. A third set of the application-specific integrated circuit chips from the first set is assembled for a second type of medical diagnostic ultrasound imaging system. The first type of medical ultrasound system is different than the second type, such as by having different hardware-based functionality. The third set includes at least two types of application-specific integrated circuits also included in the second set.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A mix and match chip set is provided for building different medical diagnostic ultrasound systems. Chips for performing different functions are used in portable as well as higher-end systems. A given application-specific integrated circuit may not span an entire range of possible systems, but may be used in two or more different systems. By providing application-specific integrated circuits (ASICs) scaled for size, power and/or performance, the same circuits may be used for multiple ranges or types of systems. For example, one standardized integrated circuit includes transmit waveform generators, transmit drivers, transmit receive switches, pre-amplification, time gain control and any sub-array or time multiplex devices. An additional integrated circuit is a receive beamformer designed to scale the number of channels and/or beams. For multiple simultaneous receive beams, an integrated circuit is provided for tracking wavefronts to better steer the receive beamformer. Accordingly, the receive beamformer ASICs may be simplified for use with lower end systems. One or more backend ASICs provide for processing from radio frequency to audio/video conversion, such as providing for detection, pre-detection processes, post-detection processes, scan conversion or other functions.

Figure 1:
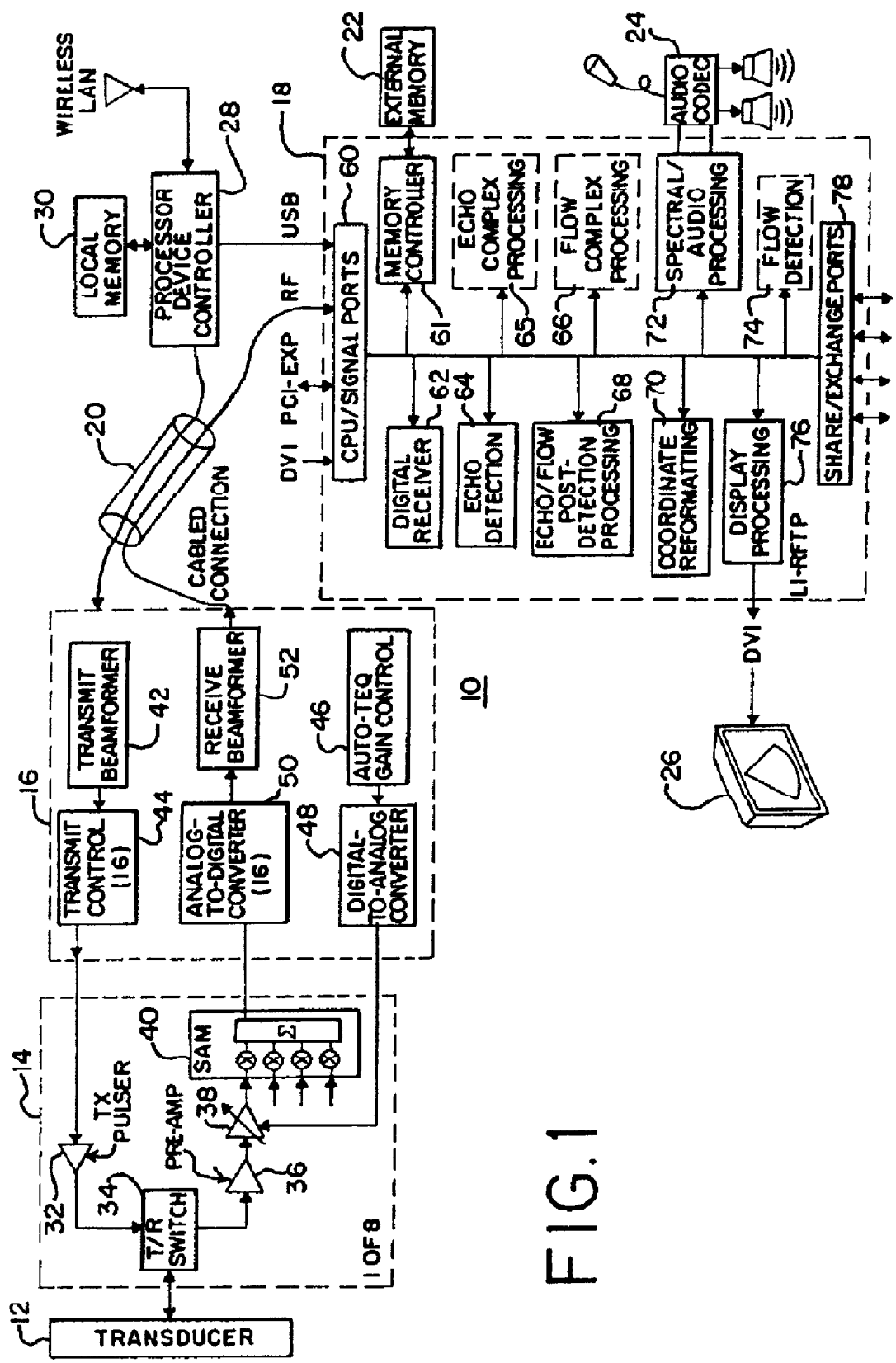
FIG. 1 is a block diagram of one embodiment of a scalable medical diagnostic ultrasound imaging system.

FIG. 1 shows one embodiment of a scalable system 10 for medical diagnostic ultrasound imaging. The system 10 includes a transducer 12, an analog frontend ASIC 14, a digital frontend ASIC 16, a backend ASIC 18, a cable 20 between the digital frontend and the backend ASICs 16, 18 or elsewhere (e.g. between the transducer 12 and the analog frontend ASIC 14), and other external devices, such as a memory 22, an audio device 24, a display device 26, a general control processor 28, and/or a memory 30 for the control processor 28. Additional, different or fewer components may be provided. For example, the digital frontend ASIC 16 is divided into two separate ASICs, one associated with transmit and the other associated with receive. As another example, the backend ASIC 18 is divided into a plurality of different ASICs, such as a prior to detection ASIC, a detection ASIC, and a post-detection ASIC.

The system 10 is a medical diagnostic ultrasound system. In one embodiment, the system 10 is a portable, such as a handheld, medical diagnostic ultrasound system with analog and digital frontend ASICs 14, 16 within a transducer head or probe. In alternative embodiments, the system 10 is a cart-based or other more complex medical diagnostic ultrasound system.

The medical diagnostic ultrasound system 10 includes an ultrasound data path between the transducer 12 and the display 26. The ultrasound data path is responsible for acquiring ultrasound data. For example, the digital frontend ASIC 16 generates transmit waveform control signals for operating a transmit pulser connected with the transducer 12. In response to echoes, a receive beamformer generates samples for detection, scan conversion or other processes to generate ultrasound data representing a scanned region. Any now known or later developed function for providing an ultrasound image performed by medical diagnostic ultrasound system may be provided along the ultrasound data path.

In the example of FIG. 1, three different application-specific integrated circuits 14, 16, 18 are provided. The analog frontend ASIC 14 includes an integrated transmit pulser 32, such as for operation from 60 to 100 volts peak. Other peak voltage may be provided, such as greater or lesser voltages. Unipolar, bipolar or other transmit pursers may be implemented. An integrated transmit and receive switch 34 switches operation of the transducer 12 between the transmit pulser 32 and a receive path with the preamplifier 36. The preamplifier 36 along with a time or depth gain control amplifier 38 are operable with a variable bias and power supply, such as providing for reduced voltages on the amplifier power rails or a programmable amplifier bias. For operation in low-end systems, reduced voltage and amplifier bias may be used to conserve power, such as for handheld battery operation. For high end systems, an increased voltage and amplifier bias may allow for better dynamic range and linearity while using the same component. Bias variation can be used to trade off dynamic range, sensitivity, frequency response and/or power dissipation to provide receive solutions over a wide range of products.

In one embodiment, a mixer and multiplexer 40 is provided for sub-array mixing, time division multiplexing, partial beamforming or other aperture reduction technique, such as disclosed in U.S. patent or Publication Nos. 5,573,001, 20050203392, 20050148878, and 20050243812, the disclosures of which are incorporated herein by reference. For spectral Doppler or high frequency transducer operation, a bypass may be provided to support high bandwidth operation. The bypass bypasses the mixer multiplexer 40. Alternatively, aperture reduction is not provided.

In one embodiment, the frontend analog ASIC 14 uses 0.13 micron mixed signal technology to achieve high circuit density. Each frontend analog ASIC 14 provides 8, a greater or lesser number of channels. For operation with large apertures, a plurality of parallel analog ASICs 14 is provided. Alternatively or additionally, one or more of the analog ASICs 14 connects with more than 8 elements of the transducer 12 and uses the sub-array mixing or aperture reduction provided by the mixer multiplexer 40. 50 milliwatts on transmit and 50 milliwatts on receive are provided for lower power operation per channel or for a low channel count system. Greater or lesser powers may be provided.

The digital frontend ASIC 16 includes a transmit beamformer 42 and transmit controller 44. The transmit beamformer 42 calculates delay and apodization profiles for one or more channels. In response to signals from the transmit beamformer 42, the transmit controller 44 generates driving signals for the transmit pulser 32. Automatic tissue equalization and gain controller 46 generates control signals for time gain control and other gain control operations. A digital-to-analog converter 48 converts the signals to analog signals for use by the adjustable gain amplifier 38. An analog-to-digital converter 50 receives analog signals and converts them to digital signals for receive beamformation by the receive beamformer 52. The receive beamformer 52 generates receive samples from a subaperture or plurality of elements using delay profiles and apodization.

In the embodiment shown in FIG. 1, the transmit beamformation, receive beamformation and gain control functions are implemented in a same frontend digital ASIC 16, but may be implemented in two or three different ASICs 16. The components of the digital frontend ASIC 16 are operable in response to various clock speeds for reducing power consumption depending on need. Different components within the digital ASIC 16 may be turned off while not in use or as a function of the type of system for which the ASIC 16 is being used. For example, about 9 watts, but greater or lesser wattage may be provided, are dissipated by operating all of the components of the digital frontend ASIC 16. In one embodiment, the digital frontend ASIC 16 is the receive beamformer disclosed in U.S. Pat. Nos. 5,369,624; 5,388,079; and 5,544,128, the disclosures of which are incorporated herein by reference.

Any number of channels may be implemented by a single digital frontend ASIC 16, such as 16 channels using single beam transmit and receive. 90 nanometer or other sized ASIC traces are used. In one embodiment, the receive beamformer 52 is operable in 1 to 4 beam simultaneous receive beam modes. For example, separate amplifiers, delays, phase rotators or other receive beamformer components are provided for each channel and each possible beam. As another example, the digital frontend ASIC 16 connects with a fewer number of channels of the transducer 12 than are available by the receive beamformer 52, such as half the number of channels for implementing two substantially simultaneous receive beams. 16 channels are used to make 4 beams while connected to four elements. By time interleaving data or aperture reduction, data from a greater number of elements may be provided for implementing receive beamformation by a single digital ASIC 16. For example, 16 channels or elements are connected providing for the interleaving of four elements on each channel. For single beam operation, 64 elements may be connected to a single digital frontend ASIC 16. Other numbers of total channels may be provided, such as 24. Using time interleaving, the input rate may be different from the output rate, such as input rate of 50 MHz and output rate of 200 MHz. Using time interleaving, a greater number of beams may be formed given the same inputs.

The digital frontend ASIC 16 is scalable, such as providing for 3, 4, 6 or 12 of the same frontend ASIC 16 operating in parallel. Greater or fewer or different numbers may be provided. Parallel operation is provided by cascaded summation of receive beamform signals. A final one of the digital frontend ASICs 16 performs the complete receive beamformation summation for passing through the cable 20 or to the backend ASIC 18. In other embodiments, two or more different ones of the digital frontend ASICs 16 connect to the same channels or overlapping channel apertures of the transducer 12 for implementing multiple substantially simultaneous receive beams.

The analog frontend ASIC 14 and the digital frontend ASIC 16 include configurable power dissipation. Dynamic range is sacrificed for lesser power. Power rails may vary, such as providing more than one rail to connect with external power sources. Bias current on amplifiers may be lowered, reducing linearity and power consumption. In a bypass mode, one of the mixers within the mixer multiplex 40 is used for low-cost continuous wave implementation.

The backend ASIC 18 is a digital ASIC with an adjustable clock rate. The plurality of signal ports 60 connect with other components, such as a USB, radio frequency, PCI, DVI and/or other inputs. Fewer or different inputs than shown may be provided. By providing different signal ports, different levels of integration are provided. The PCI interface allows for high end or higher bandwidth processing connection with the processor controller 28. USB allows for lower end or lower bandwidth control. In the embodiment shown in FIG. 1, a single backend ASIC 18 is provided for simple or low-end system 10. Two or more ASICs 18 may be provided in parallel for higher end operation.

The digital receiver 62 is operable to receive up to 80 mega samples per second, but greater or lesser rates may be provided. The digital receiver 62 implements base band filtering or processing. The memory controller 61 operates with the external memory 22 for storing data for use within the backend ASIC 18. Intensity, such as B-mode or M-mode echo detection is provided by the echo detector 64. Flow detection, such as velocity, power, or variance, is provided by the flow detector 74. Pre- and post-detection processing may be provided. For example, post-detection B-mode or flow processing is provided in component 68. For higher end operation, different aspects of the post- and pre-detection components may be turned off or enabled, altering power consumption. In-phase and quadrature information are processed prior to detection by the complex processors 65 and 66. The echo complex processor 65 and flow processor 66 operate for multiple simultaneous receive beamformation. For example, different beams are interpolated or synthesized from receive beams for increased beam density using complex processes. Scan conversion is provided by coordinate reformatter 70. A display processor 76, such as a frame buffer, outputs digital video information to the display 26. Additional, different or fewer components may be provided.

For spectral and/or M-mode processing, a wall filter, gap estimation, fast Fourier transform, audio processing and statistics computations are provided by the spectral audio processor 72. Gap estimation interpolates between temporal samples of spectral or M-mode information. Any of various statistics may be provided, such as a mean, maximum, minimum or other value. Sweeping, scrolling, or graphical trace spectral Doppler functions are provided.

The data ports 78 share data between the backend ASICs 18 used in parallel. Data processing is divided between backend ASICs 18 as a function of time or spatial location. For example, one ASIC is responsible for data processing associated with one portion of a scanned region, such as every other scan line. Where data is to be exchanged between ASICs, such as associated with filtering adjacent spatial locations, the ports 78 provide the data. Different ASICs 18 may perform different axial functions. For lateral processing, data is exchanged through the port 78. As another example, spectral Doppler operations are performed using the same data sets in each of parallel backend ASICs 18. Fourier transform processing is performed in parallel, but optimized for outputting different temporal samples. The wall filtering, gap estimation and fast Fourier transform are divided over time, such as for every other temporal sample between parallel ASICs 18. Where a given backend ASIC 18 is optimized to receive data from only the sub-apertures, the data is transferred through the port 78 to other backend ASICs 18 for fast Fournier transforming from a full sampling.

The display processor 76 includes a buffer for providing low-end graphics, such as a user name or other general system function summaries directly from the backend ASIC 18 for the display 26. For higher end displays, graphics generated by the controller 28 may be routed through the display processor 76 to the display 26. Using the coordinate reformatter 70, different resolutions may be provided for different types of data. For example, 12 mega samples per second scan conversion is provided for B-mode, velocity, variance or power imaging, 24 mega samples per second are provided for sweep, scroll and vertical scaling associated with M-mode and spectral imaging, and 80 mega samples per second are provided for color frame interpolation to generate color frames for temporal appeal (e.g., receiving 10 frames per second and interpolating 60 frames per second). Other differences in distribution of display processing with fewer or greater samples per second may be provided. In one embodiment, post-processing look-up tables, such as color maps for flow imaging, are integrated as part of the backend ASIC 18. Alternatively, one or more functions described above for the backend ASICs 18 are performed in separate ASICs or by other devices. For example, the pre- and post-detection processes are divided amongst two different ASICs. Each of the ASICs may be then scaled separately. As another example, scan conversion is provided by a different ASIC or other display processing.

Figure 2:
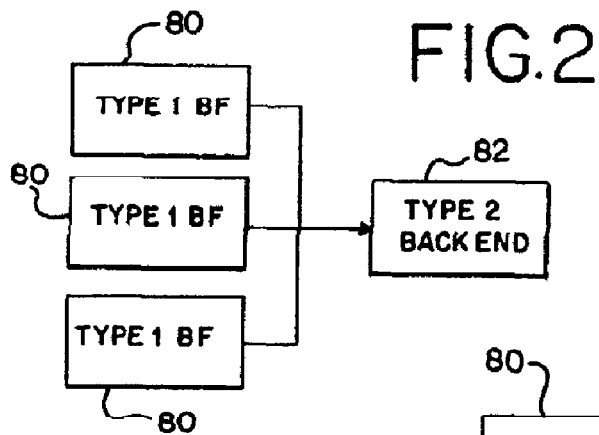
FIG. 2 is a block diagram of one embodiment of an arrangement of application-specific integrated circuits for a low-end ultrasound system.
Figure 3:
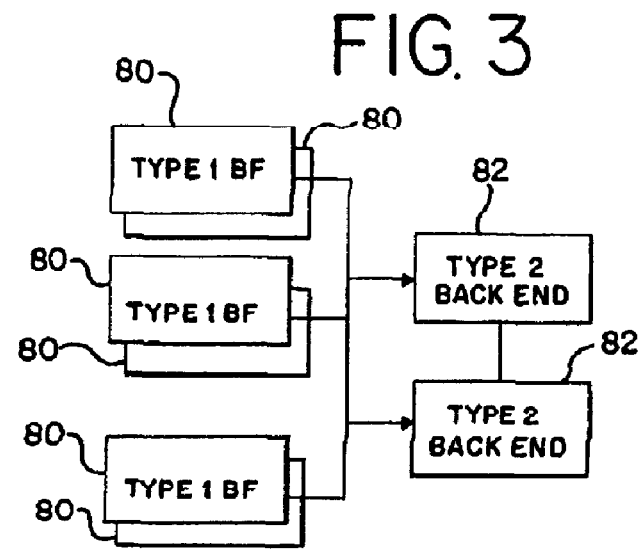
FIG. 3 is a block diagram of one embodiment of an arrangement of application-specific integrated circuits for a higher end ultrasound system.

FIGS. 2 and 3 show two embodiments of a scalable system for medical diagnostic ultrasound imaging. Each of the embodiments includes one or more of a first type of integrated circuit 80 and one or more of a second type of integrated circuit 82. Additional, different or fewer components may be provided. For example, a third type of integrated circuit common to both systems may be provided. As another example, additional or fewer of the first or second types of integrated circuits 80, 82 are provided. As yet another example, one type of integrated circuit is used in one of the systems, such as the system of FIG. 3, and not in the other system, such as the system of FIG. 2. For simplicity, additional features or components, such as transducers, displays, memories, controllers, general processors, or other components along an ultrasound data path are not shown.

The systems of FIGS. 2 and 3 use integrated circuits 80, 82 common to both systems. By using scalable integrated circuits 80, 82, different types of systems with different capabilities are provided with mixed and matched integrated circuits 80, 82. For example, FIG. 2 shows three beamformer type integrated circuits 80 being used with a single backend integrated circuit 82, and FIG. 3 shows six of the beamformer type integrated circuits 80 used with two of the backend type integrated circuits 82. Providing scalable integrated circuits 80, 82 allows for growth in the number of channels, processing bandwidth, or addition of features.

The first type of integrated circuit 80 performs one or more functions along an ultrasound data path. Different types of integrated circuits are used to distinguish between integrated circuits performing different functions. A given type of integrated circuit performs the same function and is a same device despite being used in different systems. Different systems provide different circuit arrangements or platforms. Different products may use a same system, such as a same circuit or platform provided in a different housing, but are sold through different marketing approaches, or programmed with different software.

The first type of integrated circuit 80 is operable with other ones of the same type of integrated circuit 80 or alone. For example, both FIGS. 2 and 3 show parallel operation of the same type of integrated circuit 80. In FIG. 2, the first type of integrated circuits 80 are provided in parallel operation across transmit or receive apertures or channels. In FIG. 3, parallel operation is provided across the apertures or channels as well as across a number of beams being formed using the same channels. Since the integrated circuits 80, 82 are provided along or form an ultrasound data path, the operation is provided in parallel relative to the ultrasound data path.

For scaling, the first type of integrated circuit 80 includes data connectivity between the integrated circuits 80. For example, each of the integrated circuits 80 has an input for receiving partially beamformed data and an output for outputting further partially summed or completely summed beamformed data. The input may be operable with a no connection. Cascaded receive beamforming or summation is provided to output receive beamformed samples from a final one of the first type of integrated circuits 80. In addition to scaling, the integrated circuits may be operable with different power levels. For example, different power or voltage rails are provided. As another example, different components within the integrated circuit 80 may be selectively disabled. As yet another example, amplifiers are provided with a programmable bias.

Any function along an ultrasound data path may be implemented by the first type of integrated circuit 80. In the example shown in FIGS. 2 and 3, the first type of integrated circuit 80 is the digital frontend ASIC 16 of FIG. 1. Alternatively, the first type of integrated circuit 80 implements the analog frontend ASIC 14 of FIG. 1. In yet other embodiments, the first type of integrated circuit 80 implements other functions or a subset of the functions, such as implementing receive beamforming without transmit beamforming or time gain control. For example, the first type of integrated circuit 80 implements transmit beamforming, receive beamforming, transmit and receive switching, a portion of any of the above-described functions or combinations thereof.

In one embodiment, the first type of integrated circuit 80 performs receive beamforming with a variable number of simultaneous receive beams. The same integrated circuit 80 may be connected to different channels as shown in FIGS. 2 and 3 or scaled by common connection to the same array elements for implementing additional receive beamformation as shown in FIG. 3. A single one of the first type of integrated circuits 80 may be operable with a variable number of simultaneous receive beams. For example, time division multiplexing is provided for connecting 16 or other number of inputs to 64 different channels. The receive beamform sum signal from all 64 channels is output from the single first type of integrated circuit 80. The samples represent a single beam. For generating two different receive beams, a multiplexer connects the integrated circuit 80 to only 32 channels. Since the integrated circuit 80 has capacity for 64 channels of operation, the redundant channels are used to form a separate or different receive beam in parallel or substantial simultaneously. Where a greater number of receive beams or the capability for receiving a greater number of substantially simultaneous receive beams is desired, such as associated with higher end systems, the given one of the first type of integrated circuits 80 is connected to a fewer number of channels.

Figure 4:
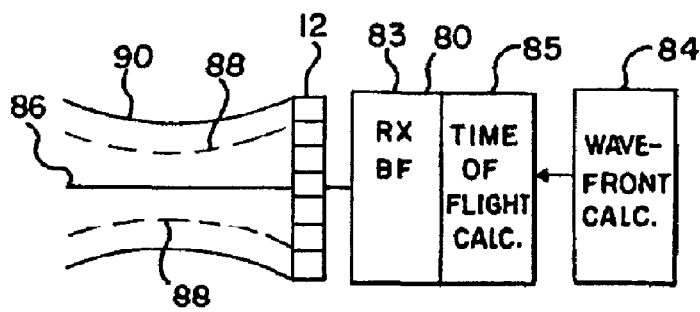
FIG. 4 is a block diagram of a receive beamformer operating with two different spatial coordinate calculators in one embodiment.

FIG. 4 shows one embodiment of a scalable system for receive beamforming with ultrasound. The first type of integrated circuit 80 includes a receive beamformer 83 and a real-time time of the flight calculator 85. The integrated circuit 80 is connectable or connects with the transducer 12. The integrated circuit 80 is operable without additional components for forming receive beams associated with an aperture along the transducer 12. A wavefront calculator 84 is connectable with the integrated circuit 80 for more complex operation. The integrated circuit 80 is a low cost fixed beamformer, and the wavefront calculator 84 alters operation of the low cost fixed beamformer for more complex information processes.

The real-time time of flight calculator 85 determines distances to acoustic sample coordinates. The time of flight calculator 85 includes a counter for counting clock pulses. The outbound time for the acoustic wavefront is common to all the elements of the array 12 and is determined with the counter. The return echo time is determined for each element of the array 12. For receive operation, dynamic focusing is provided by determining a distance to a current receive focal point for each of the elements within the aperture. Using sine, cosine or both cosine and sine functions, distance is determined as a function of element location and associated acoustic sample locations. For example, a distance from a given element to a position along a straight scan line 86 is calculated. Given the distance and the speed of sound, a time of flight relative to different acoustic sample locations along the scan line 86 is calculated. In one embodiment, the real-time time of flight calculator disclosed in U.S. Pat. No. 5,501,219, the disclosure of which is incorporated herein by reference, is used. Other time of flight calculators may be provided.

During a scan, the position of the scan line 86 is a function of scan line origin along the transducer 12 and/or angle relative to the transducer 12. The real-time time of flight calculator 85 determines the distance to each acoustic sample as needed during operation. As each scan line 86 is repositioned for scanning an object, the determined time of flight or distances may be updated through interpolation. Alternatively, the time of flight is independently calculated for each scan line. Since the beam coordinates are typically close to each other and close to the focus transmit beam, the echo path for all the beam coordinates or acoustic sample coordinates along a given scan line 86 are based on counting elapsed time and the velocity of sound.

Given a few beams and a transmit focus, the outbound transmit path is simplified to an accounting of time from the initiation of the transmit beam center or origin from the transducer 12 to the range of interest. Beam coordinates are then generated from the point of initiation along straight scan line 86 of propagation. However, if multiple receive beams are formed substantially simultaneously in response to a single transmit beam, each of the receive beams may be warped by the distribution of acoustic energy in the transmit beam. Simple time of flight calculation may not accurately model the characteristics of a coherent acoustic wavefronts affected by wavelength and aperture. Aberrations may also result in inaccuracies. For implementation in simple systems, sacrifices associated with straight line assumption for receive beamforming may be used. For more complex systems, greater accuracy or resolution may be desired. The wavefront calculator 84 implements more accurate receive beamforming. The time of flight delay is partitioned into the simple scheme provided by the time of flight calculator 85 and the more sophisticated scheme provided by the wavefront calculator 84.

The time of flight calculator 85 includes inputs or ports for receiving externally generated acoustic sample coordinates. The wavefront calculator 84 is a separate component than the first type of integrated circuit 80. If the wavefront calculator 84 is connected with the time of flight calculator 85, the reception of external acoustic sample coordinates is activated. Since a given point in space has a common outbound time of flight, a single wavefront calculator 84 may be provided for each element of the transducer 12 or all of the first type of integrated circuits 80 implementing a receive beamforming function. The wavefront calculator 84 operates independent of the number of channels or beamformer devices. The wavefront calculator 84 is an integrated circuit, ASIC, processor, controller, memory, look-up table, digital signal processor, analog circuit, digital circuit, field programmable gate array, combinations thereof or other now known or later developed device for determining acoustic sample coordinates.

Rather than a sine or cosine scaled counter, the wavefront calculator 84 determines acoustic sample coordinates along non-straight lines. For example, FIG. 4 shows receiving along two curved lines 88 generally corresponding to a curved distribution of acoustic energy associated with a transmit beam 90 along a scan line 86. The transmit wavefront is determined as a function of time, the density of the receive samples (e.g., the number of simultaneous receive beams), and the extent laterally of the acoustic energy of the transmit beam 90. By receiving multiple simultaneous receive beams distributed laterally within the transmit beam 90, one or more of the receive beams 88 is along a non-straight line. Other calculations may alternatively or additionally be performed, such as associated with determining Gaussian beam estimations or dynamically updating wavefront anomalies associated with tissue aberrations.

The wavefront calculator 84 outputs the acoustic sample coordinates to the time of flight calculator 85. The output acoustic sample coordinates changes the acoustic sample coordinates to be used by the time of flight calculator. The change is to an input coordinate instead of or as an alternative to using a coordinate determined by the time of flight calculator 85. By loading the acoustic sample coordinates determined by the wavefront calculator 84, the time of flight calculator 85 changes the acoustic sample coordinates, overriding the internal coordinate determination functions. The acoustic sample coordinates are loaded synchronously with the internal timing of the time of flight calculator 85. The outbound time of flight remains or uses the counter, and return echo time of flight is based on a distance to the acoustic sample coordinates loaded from the wavefront calculator 84.

For subsequent processing, the wavefront calculator 84 generates reconstruction coefficients for converting acoustic sample coordinates to a linear space. The coefficients are interpolation values, weighting, or a definition of the sample grid used for calculating the acoustic sample coordinates. Each sample is associated with a coefficient for reconstructing the data at a later stage, such as prior to detection or before or after any synthetic or complex sample processing. Outputting coefficients may complicate later signal processing, but allows for more simplistic implementation of the receive beamformer 83 of the first type of integrated circuit 80. The computations for beamforming tend to be more extensive given large channel counts than scaling or converting acoustic samples.

The receive beamformer 83 forms the acoustic samples as a function of distances received from the time of flight calculator 85. The acoustic samples are formed for a portion of an aperture on the transducer 12 or for the entire aperture. The real-time time of flight calculator 85 and receive beamformer 83 are operable without the wavefront calculator 84. For example, a lower cost system is implemented without the wavefront calculator 84. A higher cost system includes the wavefront calculator 84. In response to distances provided by the time of flight calculator 85 based on simple straight line geometry or more complex geometry provided by the wavefront calculator 84, the receive beamformer 83 outputs acoustic samples with or without additional reconstruction coefficients.

In alternative embodiments, the first type of integrated circuit 80 operating as a receive beamformer includes the wavefront calculation components. In yet other embodiments, a receive beamformer with database or lookup table based delay profiles is provided.

The second type of integrated circuit 82 shown in FIGS. 2 and 3 is the back end ASIC 18 of FIG. 1 or a different integrated circuit. The second type of integrated circuit 82 performs an additional function along the ultrasound data path. For example, functions include: base band processing detection, scan conversion, image processing, predetection synthesis, complex processing, scan conversion, continuous wave image processing, quantification or combinations thereof. The function performed by the second type of integrated circuit 82 is responsive to data output by the first type of integrated circuit 80. For example, acoustic samples are output by the first type of integrated circuit 80. The second type of integrated circuit 82 receives the acoustic samples and generates image data. Alternatively, the second type of integrated circuit 82 receives input data and outputs data subjective to further processing but not in a format or values for display.

The second type of integrated circuit 82 is scalable. For example, FIG. 2 shows one of the second type of integrated circuits 82, and FIG. 3 shows two of the second type of integrated circuits 82 in parallel along the ultrasound data path. Data is exchanged between different ones of the second type of integrated circuit 82 for implementing parallel processing, such as for implementing M-mode or spectral Doppler type imaging. One of the second type of integrated circuits 82 combines the information from all of the second type of integrated circuits 82 for outputting a display image. Alternatively, an additional component combines information output from the different ones of the second type of integrated circuits 82. In alternative embodiments, both low and high cost diagnostic ultrasound systems use a single one of the second type of integrated circuits 82.

The ultrasound data path provided by the first type of integrated circuit 80, the second type of integrated circuit 82 and any other integrated circuits usable in multiple systems has different complexity levels. For example, FIG. 2 represents a lower complexity level than FIG. 3. Complexity is provided by increased bandwidth, performance of additional functions, ability to operate with additional inputs, ability to operate with additional outputs, resolution, or other factors. In general, the complexity level is associated with cost. FIG. 3 represents an increased complexity for a higher cost medical diagnostic ultrasound imaging system, and FIG. 2 represents a lower complexity level associated with a lower cost medical diagnostic ultrasound imaging system. The lower complexity level is associated with a fewer number of the first type of integrated circuits 80 and/or the second type of integrated circuits 82. Different housings may be provided, such a cart based system for the more complex level of the ultrasound data path and a portable (e.g., hand-held or carryable) housing for the lower complexity level system. For more complex ultrasound data path, additional types of integrated circuits or other components not included in the low cost medical diagnostic ultrasound system are provided. For example, the wavefront calculator 84 shown in FIG. 4 is included in a higher cost medical diagnostic ultrasound imaging system but not in a lower cost medical diagnostic ultrasound imaging system. The number of the first type of integrated circuit 80 or receive beamformer components may be greater for more complex ultrasound data paths, such as associated with operation with a greater number of simultaneous receive beams.

FIGS. 1, 2 and 3 show two or three different levels of complexity. For example, FIG. 2 is a general representation of the system of FIG. 1. More than two levels of complexity and associated cost for ultrasound systems may be provided. For example, a middle cost medical diagnostic ultrasound system with a mid-complexity level of the ultrasound data path is provided. Any of the various features described above may be provided in the same, or different level than the low and high complexity level ultrasound data paths. For example, a fewer number of the first type of integrated circuits 80 are provided in the middle cost system than for a high cost system of FIG. 3, and a greater number are provided than for the low cost system of FIG. 2.

Figure 6:
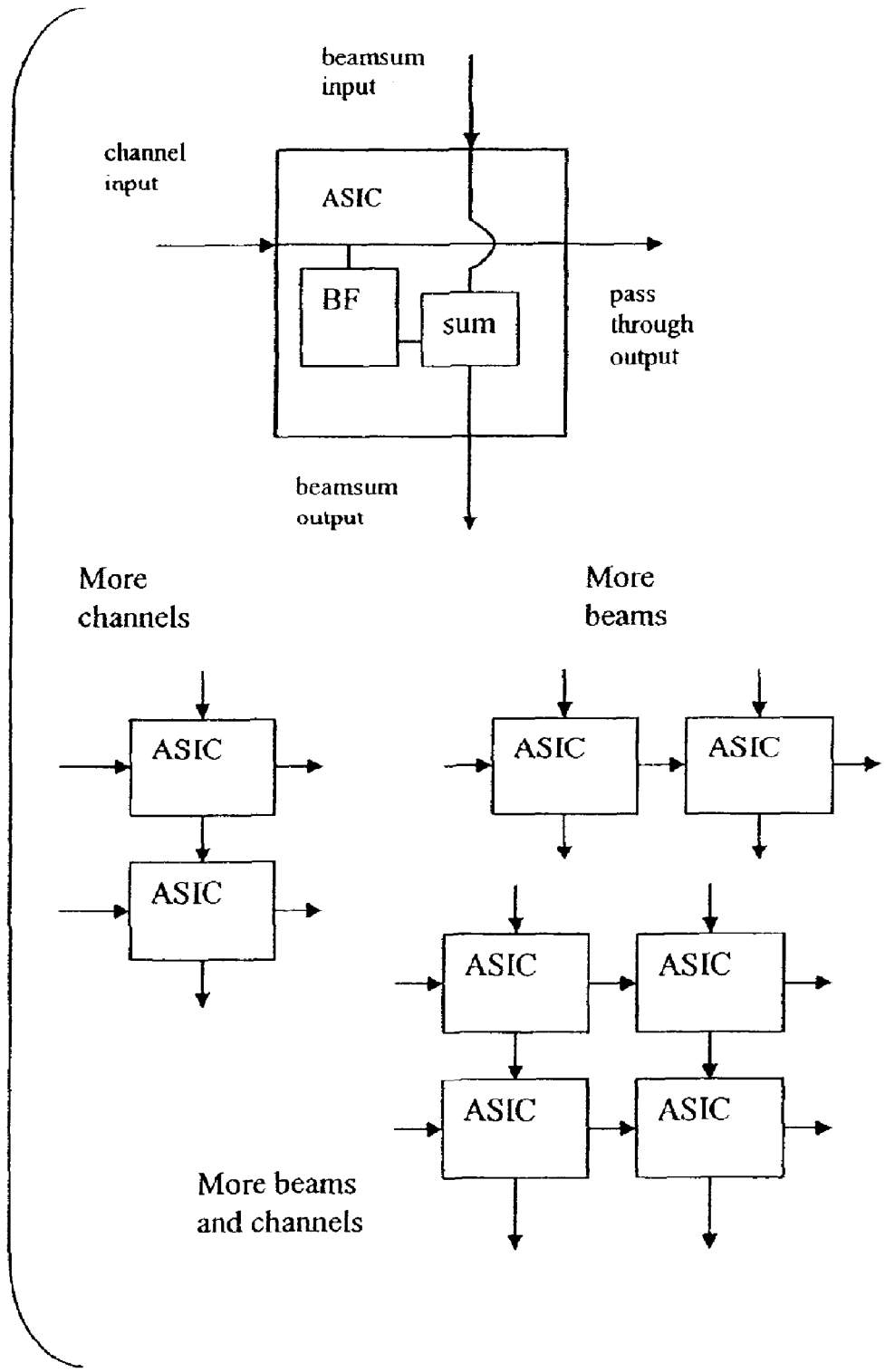
FIG. 6 is a block diagram an ASIC with scalable beam-channel product.

FIG. 6 shows a receive beamforming ASIC with a channel input, a channel output, a beamsum input and a beamsum output. The channel input connects with the beamsum output and the channel output. The channel output outputs the input signal without alteration. The beamsum output connects with a beamformer and summer for combining the channel input signals with the beamsum input signals. The ASICs are combined beamsum input to output for implementing beamforming in a simple or lower cost system. To provide formation of multiple beams using the same input channels, the ASICs are combined so that additional beams are formed from connection with the channel output (i.e., multiple columns of ASICs). The arrangement of FIG. 6 may be used in addition to the arrangement of FIG. 3.

In one example price distribution for medical diagnostic ultrasound systems, five different platforms using different selections of the same integrated circuits 80, 82 are provided. For example, table 1 shows five different levels of complexity and associated cost of medical diagnostic ultrasound imaging systems.

TABLE 1

|  | 1st price segment | 2nd | 3rd | 4th | 5th |
| --- | --- | --- | --- | --- | --- |
| TX/RX Channels | 192/192 | 96/96 | 64/64 | 48/48 | 16/32 |
| Color/flow | Y | Y | Y | Y | (power) |
| PW/CW/Aux CW | Y/Y/Y | Y/Y/Y | Y/Y/Y | Y/Y/Y | N/Y/N |
| Parallel RX beams | 4 | 4 | 2 | 2 | 1 |
| Probe elements | 192 | 192 | 192 | 128 | 64 |
| Ports-transducer connectors | 3 | 3 | 3 | 1/2 | 1 |
| Pixels | 1152/864 | 920/690 | 720/540 | 720/540 | 290/216 |
| Power | 1200 W | 800 W | 300 W | 100 W | 5 W |

In table 1, the fifth price segment is associated with a hand-held system. For the difference in the number of transmit and receive channels for the fifth price segment system, the partial beamformer, time division multiplexing, or subarray mixing are used to allow 16 analog-to-digital converters to cover 32 elements. Color or flow indication with a Y for yes indicates velocity, power and/or variance. The number of parallel receive beams indicate the maximum number of substantially simultaneously formed receive beams. The probe elements number indicates a maximum number of elements within a probe that may be connected with the system. For the fourth price segment system, the number of ports or transducer connectors varies depending on housing options, such as two ports being available with a mobile cart and only one port being available with a non-cart (e.g. suitcase size portable) system. The number of pixels indicates a resolution for display. Other distribution of features and price segments may be provided than shown in table 1.

Figure 5:
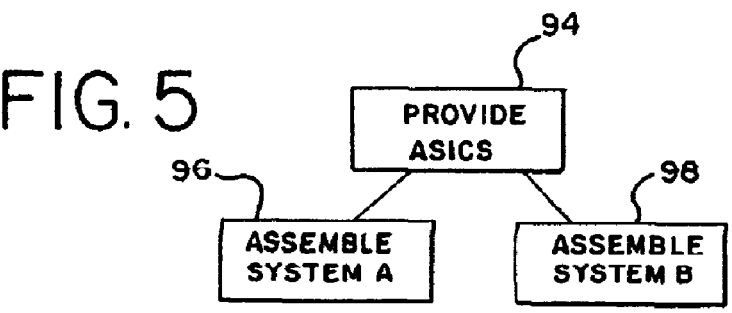
FIG. 5 is a flowchart diagram of one embodiment of a method for scaling an ultrasound system.

FIG. 5 shows one embodiment of a method for scalable manufacturing of medical diagnostic ultrasound imaging systems. Additional or different acts may be provided than shown in FIG. 5. For example, additional types of systems with different levels of complexity are assembled.

In act 94, a set of application specific integrated circuit chips is provided. Different types of chips have different ultrasound functions. The set is provided for mix and match assembling of different ultrasound systems.

In act 96, a first type of medical diagnostic ultrasound imaging system is assembled. A set of chips from the mix and match set are connected or assembled together. For example, the low cost medical diagnostic ultrasound system shown in FIG. 2 is assembled from the two, at least in part, types of integrated circuits 80, 82. For low cost systems, a fewer number of beamforming type circuits are assembled together.

In act 98, a higher cost medical diagnostic ultrasound system is assembled from the same types of application specific integrated circuit chips. For example, the system shown in FIG. 3 is assembled. More of the beamforming type of integrated circuits are provided. Additional integrated circuits not in a lower end system may be provided, such as including the wavefront calculator 84 shown in FIG. 4.

By using a same collection of types of integrated circuits, the integrated circuit chips used for the different types of medical diagnostic ultrasound systems include common integrated circuit chips. For example, those systems use the same integrated receive beamformer and integrated detection type chips. To further differentiate the systems, the application specific integrated circuit chips used in the different systems may operate at different power levels, with different numbers of maximum simultaneous receive beams or other features or functions.

The same types of application specific integrated circuit chips may be assembled into yet other medical diagnostic ultrasound imaging systems. Different numbers of the same chips or different combinations of the provided application specific integrated circuit chips are connected together for implementing different medical diagnostic ultrasound imaging systems or platforms. The same types of chips are used in different systems, such as providing for two, three, four or more types of common application specific integrated circuit chips in different ultrasound imaging platforms.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for scalable manufacturing of medical diagnostic ultrasound imaging systems, the method comprising:
   providing a first set of application specific integrated circuit chips having ultrasound functions;
   assembling a second set of the application specific integrated circuit chips from the first set for a first type of medical diagnostic ultrasound imaging system; and
   assembling a third set of the application specific integrated circuit chips from the first set for a second type of medical diagnostic ultrasound imaging system, the first type of medical diagnostic ultrasound imaging system different than the second type;
   wherein the third set includes at least two types of application specific integrated circuit chips also included in the second set;
   wherein assembling the second set comprises assembling a lower cost medical diagnostic ultrasound imaging system, and assembling the third set comprises assembling a higher cost medical diagnostic ultrasound imaging system.

2. The method of claim 1 wherein assembling the second set comprises assembling with fewer of a beamforming type of application specific integrated circuits for the lower cost medical diagnostic ultrasound imaging system and assembling the third set comprises assembling with more of the beamforming type of application specific integrated circuits for the higher cost medical diagnostic ultrasound imaging system.

3. The method of claim 2 where assembling the second and third sets comprise setting the beamforming type of application specific integrated circuits for a fewer number of maximum simultaneous receive beams for the lower cost medical diagnostic ultrasound imaging system than for the higher cost medical diagnostic ultrasound imaging system.

4. The method of claim 1 wherein assembling the third set comprises including at least one type of application specific integrated circuit not in the second set.

5. The method of claim 1 wherein assembling the second and third sets comprise assembling a plurality of receive beamforming application specific integrated circuits and one or more detection, scan conversion, image processing or combination thereof application specific integrated circuits.

6. The method of claim 1 further comprising assembling a fourth set of the application specific integrated circuit chips from the first set for a third type of medical diagnostic ultrasound imaging system, the third type of medical diagnostic ultrasound imaging system different than the first and second types;
   wherein the fourth set includes at least two types of application specific integrated circuit chips also included in the second set.

7. The method of claim 1 wherein the lower cost medical diagnostic ultrasound imaging system is a portable system and the higher cost medical diagnostic ultrasound imaging system is a cart based system.

8. The method of claim 1 wherein the lower cost medical diagnostic ultrasound imaging system has fewer transducer connector ports, a lesser image resolution capability and less power than the higher cost medical diagnostic ultrasound imaging system.

9. A method for scalable manufacturing of medical diagnostic ultrasound imaging systems, the method comprising:
   providing a first set of application specific integrated circuit chips having ultrasound functions;
   assembling a second set of the application specific integrated circuit chips from the first set for a first type of medical diagnostic ultrasound imaging system; and
   assembling a third set of the application specific integrated circuit chips from the first set for a second type of medical diagnostic ultrasound imaging system, the first type of medical diagnostic ultrasound imaging system different than the second type;
   wherein the third set includes at least two types of application specific integrated circuit chips also included in the second set;
   wherein at least one of the types of the application specific integrated circuit chips is operable with different levels of power supply.

10. A method for scalable manufacturing of medical diagnostic ultrasound imaging systems, the method comprising:
   providing a first set of application specific integrated circuit chips having ultrasound functions;
   assembling a second set of the application specific integrated circuit chips from the first set for a first type of medical diagnostic ultrasound imaging system; and
   assembling a third set of the application specific integrated circuit chips from the first set for a second type of medical diagnostic ultrasound imaging system, the first type of medical diagnostic ultrasound imaging system different than the second type;
   wherein the third set includes at least two types of application specific integrated circuit chips also included in the second set;

wherein assembling the second and third sets comprise summing a beamsum input with a channel input and passing the channel input to a channel output without alteration.

11. A method for scalable manufacturing of medical diagnostic ultrasound imaging systems, the method comprising:
providing a first set of application specific integrated circuit chips having ultrasound functions;
assembling a second set of the application specific integrated circuit chips from the first set for a first type of medical diagnostic ultrasound imaging system; and
assembling a third set of the application specific integrated circuit chips from the first set for a second type of medical diagnostic ultrasound imaging system, the first type of medical diagnostic ultrasound imaging system different than the second type;
wherein the third set includes at least two types of application specific integrated circuit chips also included in the second set;
wherein the chips of the first set include a real-time time of flight calculator operable to determine distances to acoustic sample coordinates, a wavefront calculator operable to change the acoustic sample coordinates to positions along a non-straight line, and a receive beamformer operable to form acoustic samples as a function of the distances.

12. The method of claim 11 wherein the real-time time of flight calculator and receive beamformer are operable without the wavefront calculator.

13. The method of claim 12 wherein assembling the second set comprises assembling a lower cost medical diagnostic ultrasound imaging system, and assembling the third set comprises assembling a higher cost medical diagnostic ultrasound imaging system, wherein the higher cost system including the wavefront calculator and wherein the lower cost system is without the wavefront calculator.

14. The method of claim 11 wherein the real-time time of flight calculator is operable to determine distances as a cosine, sine or cosine and sine function of element coordinates to the acoustic sample coordinates.

15. The method of claim 11 wherein the wavefront calculator is operable to override the acoustic sample coordinates as a function of multiple simultaneous receive beams.

16. The method of claim 11 wherein the wavefront calculator is operable to override the acoustic sample coordinates as a function of aberrations.

17. The method of claim 11 wherein the wavefront calculator is operable to override the acoustic sample coordinates as a function of a Gaussian beam wavefront.

18. The method of claim 11 wherein the receive beamformer and real-time time of flight calculator are operable to output the acoustic samples and wherein the wavefront calculator is operable to provide reconstruction coefficients for converting the acoustic sample coordinates to a linear space.

19. The method of claim 11 wherein the wavefront calculator is operable to change the acoustic sample coordinates as a function of a location as a function of time, a lateral density of samples and a lateral extent.

* * * * *